US008715329B2

(12) United States Patent
Robinson et al.

(10) Patent No.: US 8,715,329 B2
(45) Date of Patent: May 6, 2014

(54) THERMAL TREATMENT DEVICE

(75) Inventors: Ronni L. Robinson, Ambler, PA (US);
Harry S. Sowden, Glenside, PA (US);
Leo B. Kriksunov, Glenside, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 639 days.

(21) Appl. No.: 12/391,337

(22) Filed: Feb. 24, 2009

(65) Prior Publication Data
US 2009/0222072 A1 Sep. 3, 2009

Related U.S. Application Data

(60) Provisional application No. 61/031,163, filed on Feb. 25, 2008.

(51) Int. Cl.
*A61F 7/00* (2006.01)
*A61F 7/12* (2006.01)

(52) U.S. Cl.
USPC .............................. 607/96; 607/108; 607/112

(58) Field of Classification Search
USPC ................................................... 607/96–114
See application file for complete search history.

(56) References Cited

U.S. PATENT DOCUMENTS

| 912,527 | A | | 2/1909 | Batter |
| 1,539,299 | A | * | 5/1925 | Cheney ........................... 601/20 |
| 1,703,811 | A | | 2/1929 | Blum |
| 3,170,459 | A | | 2/1965 | Phipps et al. |
| 3,327,713 | A | | 6/1967 | Eidus |
| 4,242,715 | A | | 12/1980 | Laird |
| 4,259,965 | A | | 4/1981 | Fukuda et al. |
| 4,479,495 | A | | 10/1984 | Isaacson |
| 4,592,358 | A | | 6/1986 | Westplate |
| 4,685,442 | A | | 8/1987 | Cieslak |
| 4,702,235 | A | | 10/1987 | Hong |
| 4,846,176 | A | | 7/1989 | Golden |
| 5,023,430 | A | | 6/1991 | Brekkestran et al. |
| 5,179,942 | A | | 1/1993 | Drulias |
| 5,302,806 | A | | 4/1994 | Simmons et al. |
| 5,312,350 | A | | 5/1994 | Jacobs |
| 5,336,255 | A | | 8/1994 | Kanare et al. |
| 5,445,647 | A | | 8/1995 | Choy |
| 5,484,366 | A | | 1/1996 | Wilkinson |
| 5,534,021 | A | | 7/1996 | Dvoretzky et al. |
| 5,605,144 | A | | 2/1997 | Simmons et al. |
| 5,665,057 | A | | 9/1997 | Murphy |
| 5,695,520 | A | | 12/1997 | Bruckner et al. |
| 5,741,318 | A | | 4/1998 | Ouellette |
| 5,848,981 | A | | 12/1998 | Herbranson |
| 5,918,590 | A | | 7/1999 | Burkett et al. |
| 5,925,072 | A | | 7/1999 | Cramer et al. |
| 5,928,275 | A | | 7/1999 | Yates et al. |

(Continued)

FOREIGN PATENT DOCUMENTS

| CH | 245959 A | 12/1946 |
| DE | 4410702 A | 10/1995 |

(Continued)

*Primary Examiner* — Matthew F Desanto
(74) *Attorney, Agent, or Firm* — Victor Tsu

(57) ABSTRACT

The present invention is directed to a reusable pain relieving treatment device, such as a belt, and a disposable thermal device having one or more thermally conductive components that extend from a surface of the device and are capable of transferring heat, cold or vibrations from disposable or reusable devices to targeted sections of the user's body.

18 Claims, 3 Drawing Sheets

(56) References Cited

U.S. PATENT DOCUMENTS

| | | |
|---|---|---|
| 6,027,521 A | 2/2000 | Ourada |
| 6,065,154 A | 5/2000 | Hulings et al. |
| 6,074,413 A | 6/2000 | Davis et al. |
| 6,102,875 A | 8/2000 | Jones |
| 6,146,342 A | 11/2000 | Glen |
| 6,206,909 B1 | 3/2001 | Hanada et al. |
| 6,309,273 B1 | 10/2001 | Kim |
| 6,409,748 B1 | 6/2002 | DeCarlo et al. |
| 6,416,534 B1 | 7/2002 | Montagnino et al. |
| 6,419,650 B1 | 7/2002 | Ryan et al. |
| 6,425,913 B1 | 7/2002 | Chao |
| 6,497,720 B1 | 12/2002 | Augustine et al. |
| 6,549,411 B1 | 4/2003 | Herbert |
| 6,567,696 B2 | 5/2003 | Voznesensky et al. |
| 6,623,419 B1 | 9/2003 | Smith et al. |
| 6,711,750 B1* | 3/2004 | Yoo ................................. 2/338 |
| 6,840,955 B2 | 1/2005 | Ein |
| 7,077,858 B2* | 7/2006 | Fletcher et al. ............... 607/104 |
| 7,147,610 B2 | 12/2006 | Maalouf |
| D559,473 S | 1/2008 | Nguyen |
| 7,399,484 B2 | 7/2008 | Ellefson et al. |
| 7,637,883 B2 | 12/2009 | Nyi |
| 7,781,051 B2 | 8/2010 | Burr et al. |
| 7,889,502 B1 | 2/2011 | Reis et al. |
| 8,021,406 B2 | 9/2011 | Cazzini et al. |
| 2002/0086204 A1 | 7/2002 | Rock et al. |
| 2002/0156509 A1 | 10/2002 | Cheung |
| 2003/0014096 A1 | 1/2003 | Burkhart |
| 2003/0125648 A1 | 7/2003 | Leason et al. |
| 2004/0082886 A1 | 4/2004 | Timpson |
| 2004/0217325 A1 | 11/2004 | Usui et al. |
| 2005/0049526 A1 | 3/2005 | Baer |
| 2005/0145372 A1 | 7/2005 | Noel |
| 2006/0258962 A1* | 11/2006 | Kopanic et al. ................. 601/15 |
| 2007/0106356 A1* | 5/2007 | Carstens ....................... 607/112 |
| 2009/0163984 A1 | 6/2009 | Robinson et al. |
| 2010/0161014 A1 | 6/2010 | Lynch et al. |

FOREIGN PATENT DOCUMENTS

| | | |
|---|---|---|
| EP | 1332740 A | 8/2003 |
| EP | 1332741 A | 8/2003 |
| EP | 1649841 A | 4/2006 |
| FR | 2408344 A | 6/1979 |
| FR | 2708196 A | 7/1993 |
| GB | 2353711 A | 3/2001 |
| JP | 10099408 A | 4/1998 |
| RU | 2093117 C1 | 10/1997 |
| RU | 28954 U1 | 4/2003 |
| WO | 97/01312 A | 1/1997 |
| WO | 2008/006018 A | 1/2008 |
| WO | WO 2008/072099 A1 | 6/2008 |
| WO | 2009/108611 A | 9/2009 |

* cited by examiner

THERMAL TREATMENT DEVICE

CROSS-REFERENCE TO RELATED APPLICATION

The present application claims the benefit of priority to U.S. Provisional Application Ser. No. 61/031,163, filed Feb. 25, 2008, the contents of which are completely incorporated by reference.

BACKGROUND OF THE INVENTION

For patients with aching muscles and sore joints, the application of heat can decrease the viscosity of fluids, loosen stiff muscles, improve blood flow to the affected area, facilitating tissue repair, and creating a feeling of relaxation. For some acute injuries, the application of cold can numb pain, constrict blood vessels and mitigate the inflammatory response. The application of heat to the skin as a means to penetrate deeper into tissues has historically been used for pain relief of muscles and joints, as well as for the treatment of certain inflammatory conditions. The application of cold materials to the skin has also been used for similar treatments, especially for treating inflammatory responses such as joint inflammation.

Traditional heating devices have, in some instances, generated heat using chemical formulations, such as iron powder formulations, that oxidize when exposed to air. Commercially available thermal chemical formulation products are mainly categorized with disposable heat patches, which are available as loosely formed fabric thermally active components filled with the exothermic composition. An alternate means of providing heat is by way of electrical heating elements that are attached to a power source. Since the desired time of use is often longer than 4 hours, in the case of an electrical source, the power source typically used in these types of devices is either an electrical wall outlet or a battery.

Other chemical heating devices include those products that incorporate heating portions into fabrics that can conform or are shaped to fit various parts of the body, such as the knee or the back as shown in U.S. Pat. No. 6,074,413. In these cases, typically the entire product, including the garment and the heat providing exothermic formulation materials, are disposable because they are incorporated into a unitary product. The chemical heating portion is not removable from such a unitary product, and therefore, the entire device is designed to be disposed following use. Each use can typically last for 6 to 12 hours, and a user can use 2-3 of these products over a 24-hour period. These types of products have the disadvantage of having loose powder formulations that do not always adequately conform to parts of the skin and do not conduct heat thoroughly to the skin since a woven or non-woven fabric surface is in contact with the skin.

Other types of devices, such as those shown in U.S. Pat. No. 5,484,366, exemplify elements that are not disposable, such as using a back belt with gel insert containers. In such a device the gel-inserts must be manually re-heated or cooled, taking more active participation by the user in order to be reusable. Similarly, the device shown in U.S. Pat. No. 6,416,534 uses a back belt with a flexible fabric, and a gel insert that is reheated using electrical heat. This type of device also involves active participation on the part of the user and a potential lag time in order to heat the gel-insert. U.S. Pat. No. 6,074,413 is directed to a disposable thermal back wrap having one or more thermal inserts comprising a plurality of heat cells, wherein heat is applied to specific areas of the user's back, for pain relief.

U.S. Pat. No. 5,605,144 is directed to a heating garment with pouch for accommodating inserted chemical heating inserts that are air activated.

U.S. Pat. No. 5,484,366 is directed to an aerobic/cross training exercise belt. The belt comprises a straight piece of material having a fastener on each end whereby the ends can be fastened together to form a closed belt. A back lumbar support is connected to the rear body of the belt. The back lumbar support has at least one pocket to mount chemical gel-inserts whereby the user would have a thermal application to the lumbar area while wear wearing the belt. The gel inserts can be heated or cooled to the desired temperature. U.S. Pat. No. 6,623,419 is directed to a therapeutic back belt and related method of manufacture. The belt includes magnets that are secured to the belt and thermally active gel material. U.S. Pat. No. 5,179,942 is directed to a lumbar support therapeutic heat/cooling/air belt. The support has one pocket in the lower back section that is capable of receiving a insert to create a thermal change or provide air for support purposes.

Additional devices have also been disclosed, as shown in U.S. Pat. No. 7,147,610, that incorporate massaging elements with the heating elements so that they are conveniently available in a single device. Such a device involves excess bulk, is non-discreet and requires the use of external power sources (i.e. a junction box) since the heating and massaging element require the use of electrical power. In addition, although the parts are reusable, electrical elements tend to be non-washable. Published U.S. Patent Application 2004/0082886 is directed to a therapeutic device for relieving pain and stress in the hands and feet. The portable device provides heat and vibratory therapies for the hand or foot.

U.S. Pat. No. 5,925,072 is directed to a disposable elastic thermal insert wherein iron powder based exothermic compositions are segmented into individual portions and integrated into a back belt. In this composition, the thermal conductivity is not optimized since the composition is separated from the skin by a fabric barrier. U.S. Pat. No. 5,918,590 is directed to a specific heat cell unit comprising an iron powder based exothermic composition, wherein a specific exothermic formulation and pocket fill volume are defined.

U.S. Pat. No. 6,146,342 is directed to massage pad having a plurality of randomly actuated pressure inducing elements. The apparatus massages the body by subjecting the body to impacts from reciprocating plungers. The plungers are secured in a flat array within a flexible pad. Each plunger has an associated solenoid device that alternately causes the plunger to project from the pad and to retract within the pad. An electrical circuit includes a power cord and plug assembly, manual controls disposed serially on the cord and plug assembly, and a controller generating operating signals randomly to the solenoids. A heating element is optionally included in the flexible pad, with a suitable controller provided among the controls.

Still other types of devices, as shown in U.S. Pat. No. 7,077,858, include those that use flexible heat exchangers to distribute cooling and heating agents to the skin utilizing electrical heat. U.S. Pat. No. 6,409,748 is directed to a heating pad with removable gel insert that provides rapid initial warming. U.S. Pat. No. 4,846,176 is directed to a thermal bandage having a conformable region that can be placed against the skin to uniformly heat or cool the contacted skin area.

SUMMARY OF THE INVENTION

Figure 1A:
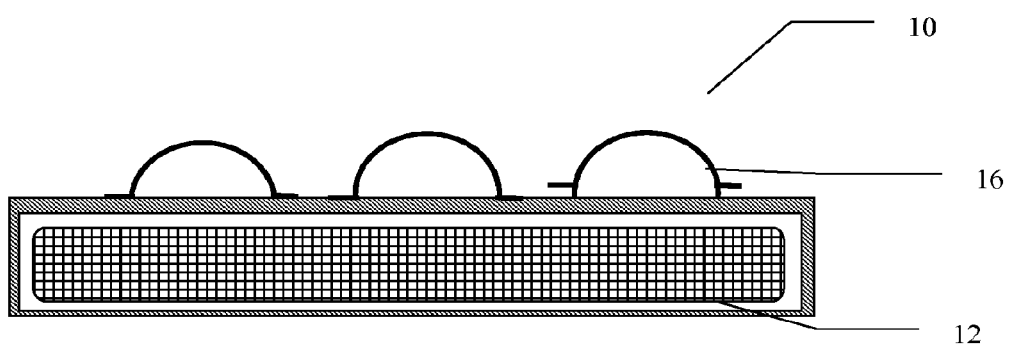
FIG. 1A is a side view of a heat treatment insert having thermally conductive massaging members.

The present invention relates to a thermal insert to be worn in close proximity to the skin of a human, and includes methods for providing a massaging and heating sensation to human skin, methods for treating muscle aches and pains in a human, as well as a therapeutic device comprising a thermal insert. The thermal inserts, devices, and methods of the present invention are useful in managing muscle and joint pain.

DETAILED DESCRIPTION OF THE INVENTION

The present invention relates to a thermal insert to be worn in a garment in close contact with the skin of a human. The present invention also provides a therapeutic device comprising a thermal insert and a garment. The present invention also provides methods for treating muscle aches and pains in a human.

The thermal device of the present invention will typically be worn in a garment. Suitable garments include belts, back belts, back wraps, sleeves, knee sleeves, elbow sleeves, knee or elbow wraps or supports, shoulder vest, shoulder support, wrist sleeve, wrist support, ankle sleeve, ankle wrap, foot support, sock, glove, hand support, or other braces and supports typically used to stabilize a joint. Suitable garments also include articles designed to adhere to the skin, such as a patch. The garment can be re-usable, e.g. constructed from washable fabric, such as a nylon-spandex fabric. Alternately, the garment can be disposable, e.g. constructed from non-woven materials. The garment preferably comprises a pocket for holding the thermal insert. The pocket is preferably constructed of a breathable and porous fabric, and attached to the garment on the surface that will be worn next to the skin.

In one particular embodiment, the pocket shape is contoured similarly to the shape of the thermal insert. In embodiments wherein the garment is designed to adhere to the skin, adhesive can be applied continuously over one surface of the patch-style garment, or adhesive can be applied discontinuously to the edges of the garment. The adhesive can be designed to adhere to the skin, or alternately can be designed to adhere to the interior of the user's clothing. The patch-style garment can be shaped like a sleeve or tube for inserting the thermal insert, or can be a flat piece of fabric with attached pocket. In one embodiment, the patch-style garment is constructed from a disposable, breathable, non-woven fabric.

The thermal insert of the present invention comprises a thermally active component, and a thermally conductive component. The thermally active component delivers heat or cold for therapeutic purposes. The thermally conductive component improves the efficiency of delivery of said heat or cold, enhancing the experience of the user.

In one embodiment, the thermal reservoir can comprise a thermally active composition: a component, material or combination of materials that activates upon the addition of heat or cold, thereby retaining the heat or cold; a thermal fill composition, or combinations thereof. In one embodiment, the thermal reservoir comprises an enclosure (shown as 14 in FIGS. 2 and 3) for said thermal composition.

The thermal reservoir comprises a thermal composition that can be any suitable material for either generating, or holding heat or for maintaining a low (cold) temperature. In one embodiment, the thermal composition emits heat from about 1 to about 10 degrees Celsius above the skin surface temperature of a human. In an alternate embodiment, the thermal fill material maintains a temperature from about 1 to about 100 degrees Celsius lower than the skin surface temperature of a human.

In one particular embodiment, the thermal reservoir comprises thermal fill materials that are a mixture of substances that react exothermically. For example, several commercial hand warmers and therapeutic heat products contain an iron powder based mixture that liberates heat as the iron is oxidized upon exposure to air. These types of systems are described in detail in for example, U.S. Pat. No. 5,918,590. It is known in the art to formulate these mixtures to maintain a temperature of at least about 40 degrees Celsius for at least 4 hours, and up to 24 hours, for example, for at least about 8 hours, e.g. for at least about 10 hours, say for at least about 12 hours, or for at least about 16 hours.

In another embodiment, the thermal reservoir comprises a thermal fill material which is a microwavable heat retaining material. Suitable heat retaining fill materials include rice, corn, barley, cherry stones, starch-based synthetic pellets, and the like. Such materials typically retain a suitable level of heat for about 20 to about 60 minutes.

In another embodiment, the thermal reservoir comprises thermally active component can comprise electrically heated or electrically cooled articles, such as a resistive heater, or a thermoelectric based cooling and heating element, such as Peltier element.

In certain embodiments, the temperature contrast measured by a thermocouple inserted between an individual's skin and the thermally conductive member of the thermal insert of this invention is 38° C., 40° C., 41° C., 45° C., or 50° C.

In another embodiment, the thermal reservoir comprises a thermal fill material that is a freezable liquid or gel at room temperature. Upon storage in a freezer, the material solidifies and maintains a temperature of less than about 5 degrees Celsius for about 20 to about 90 minutes. In one such embodiment, the temperature measured by a thermocouple inserted between the individual's skin and the thermally conductive member of the thermal insert of this invention is 5° C., 10° C., 20° C., 25° C., or 30° C.

In one embodiment the thermal reservoir is a material or combination of materials which are solid at temperatures from about −20° C. to 20° C., or at about 0° C. In one embodiment the thermal reservoir is substantially free of materials that are combustible, flammable, or volatile. As used herein, "substantially free" is defined as less than 1 percent by weight of the thermal reservoir. Combustible materials include but are not limited to fuels such as alcohols such as ethanol, methanol and butanol; or fuels such as lighter fluids, kerosene, lantern oils, and mixtures thereof.

In one embodiment, the thermal reservoir comprises an enclosure. The optional enclosure for the thermal reservoir can be any material that contains the thermal reservoir or the thermal fill composition within the thermal reservoir. In one embodiment, the enclosure is a pouch constructed of breathable non-woven fabric. In another embodiment, the enclosure is a water-tight polymer film pouch for holding a freezable liquid. In another embodiment, the enclosure is constructed from woven textile fabric. In certain embodiments, the enclosure is a pouch having one surface formed from a relatively non-conductive fabric, and a second surface comprising the thermally conductive component.

The thermally conductive component has a thermal conductivity of at least about 10 W/mK, such as at least about 100 W/mK, say from about 150 W/mK to about 250 W/mK. For sake of comparison, the thermal conductivity for some representative materials is shown below:

| | |
|---|---|
| Polypropylene: | 0.12 W/mK |
| Stainless steel: | 21 W/mK |
| Aluminum: | 221 W/mK |

Suitable materials for forming the thermally conductive component include metals, such as aluminum, copper, silver, steel, and metal alloys of aluminum, copper, silver, steel, and combinations thereof, non-metallic thermally conductive materials, such as carbon-based materials, including graphite, glassy carbon, thermally conductive plastics, polymers, rubber, or such as conductive textiles, composites, ceramics, and mixtures thereof. Optionally, these thermally conductive components can contain wires or fibers comprising the metals described above in order to make them more thermally conductive. Preferably, the thermally conductive component is non-reactive with the thermal fill composition, or with air and moisture.

In embodiments in which the thermal reservoir comprises a thermal fill material that is activated by microwave, the thermally conductive component must be designed accordingly. For example, in one version of this embodiment the thermally conductive component comprises a non-metallic substance, such as ceramic. In another version of this embodiment, the thermally conductive component comprises a plastic portion that has a shielded metallic surface that is not exposed to the energy of the microwave. In yet another version of this embodiment, the thermally conductive component is packaged separately from the thermally active component, along with means (such as an adhesive) for attaching the thermally conductive component to the thermally active component after microwave heating.

In certain preferred embodiments, the thermally conductive component has a portion of its surface that is raised above the plane of the thermally active component. In certain such embodiments, the raised portions have a rounded shape. As used herein, rounded shape is defined as elliptical, semi-elliptical, semi-circular, or circular. In certain such embodiments the raised portions of the conductive surface are raised by from about 2 millimeters to about 3 centimeters from the surface of the active component. The raised portions of the surface can advantageously provide a massaging sensation when held against the skin. For example, when the thermal insert of the present invention is worn in a back belt, with the raised portions of the thermally conductive component in close contact with the skin, the raised portions can give the sensation of fingers, massaging the skin as the wearer moves. In one particular embodiment, all or a portion of the thermally conductive component can be configured to rotate around a supporting element, or within a socket. In this embodiment, the thermally conductive massaging element can shaped as a cylinder, sphere, octahedron, dodecahedron, or any suitable rotatable shape.

In the broader embodiment, the thermally conductive component can be of a various shapes, including round, semispherical, elongated, ellipsoidal, cylindrical, star shaped, mushroom shaped, or similar shapes. According to an embodiment of the present invention, the shapes of the thermally conductive component at the interfaces to the individual's body can be flat or non-flat, including but not limited to semi-spherical, pyramidal, conical, concave, convex, bumped, or contain an array of smaller shapes, e.g. semi-spherical protrusions.

In certain embodiments, the thermally conductive component can form a single, continuous layer on the surface of the thermally active component. For example, the thermally conductive component can be a single piece of foil having deep drawn protrusions in its surface. In certain other embodiments, the thermally conductive component can be discontinuously arranged upon a surface of the thermally active component. For example, the thermally conductive component can be a single piece of foil having cut-outs to enhance aesthetics or breathability of the thermal insert, or the thermally conductive component can comprise a plurality of individual metallic parts, individually adhered to the surface of the enclosure for the thermal fill composition. In embodiments where the thermally conductive component is a piece of foil, the thickness of the foil can be from about 0.006 mm to about 0.3 mm, or about 0.01 mm to about 0.2 mm. The foil can be present on a single surface of the thermal reservoir, on two or more surfaces or surrounding the entire thermal reservoir.

In certain embodiments, the thermally conductive component can itself form a portion of the enclosure for the thermal fill composition. For example, the thermal fill composition can be a powder enclosed in a pouch-type structure, one surface of which comprises a porous non-woven fabric, and another surface of which comprises a metallic thermally conductive material, or the thermal fill composition can be a freezable liquid or gel enclosed in a pouch-type structure, one surface of which comprises a polymeric water-tight film, and another surface of which comprises a metallic film.

Figure 3:
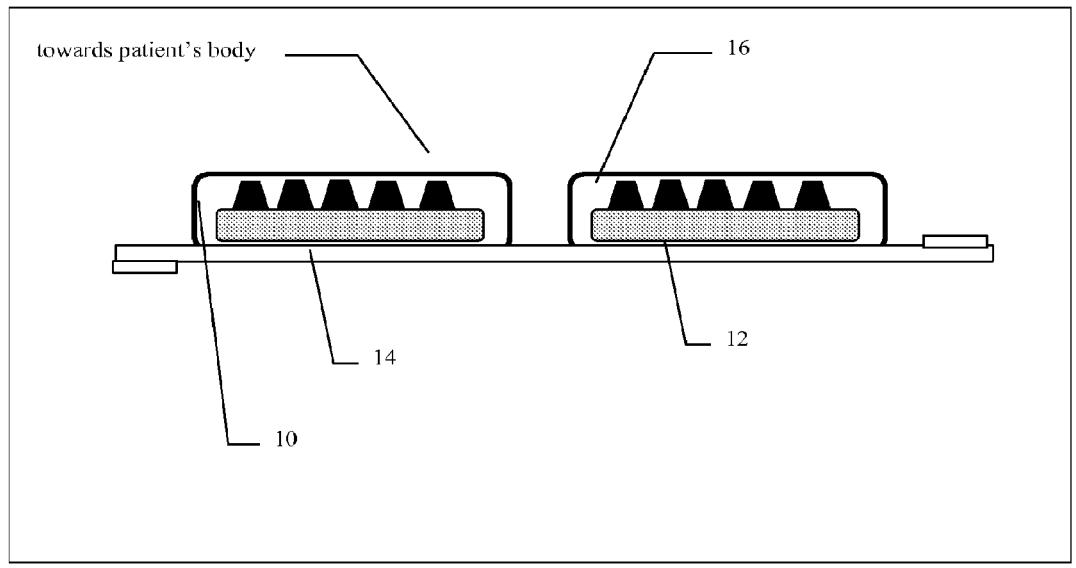
FIG. 3 is a side view of a heat treatment belt having a thermal insert
Figure 4:
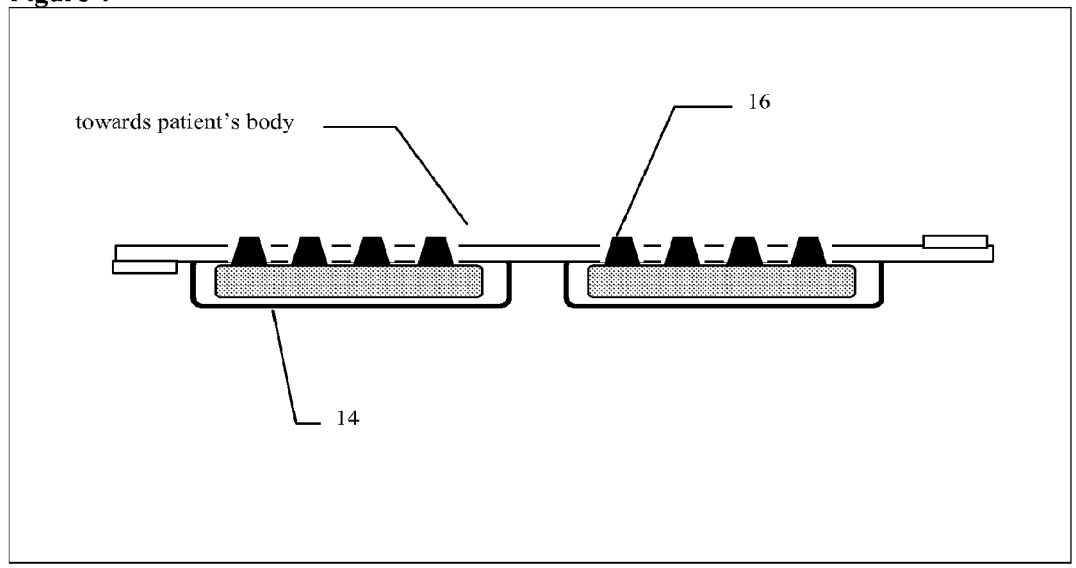
FIG. 4 is a side view of a heat treatment belt having a thermal insert with cutouts in the belt for the thermally conductive component.

In certain embodiments, the thermally conductive component can be all or partially contained within the enclosure for the thermal reservoir as exemplified in FIGS. 3 and 4. For example, the thermally conductive component can be in the form of pellets having a diameter from about 1 to about 20 millimeters, e.g. from about 2 to about 10 millimeters, which are dispersed throughout the thermal fill composition.

In another such embodiment, the thermal insert can be configured so that a portion of the thermally conductive component is in contact with the thermal fill material and the interior of the enclosure, while another portion of the thermally conductive component protrudes through openings in the enclosure to form an exterior surface.

Figure 2:
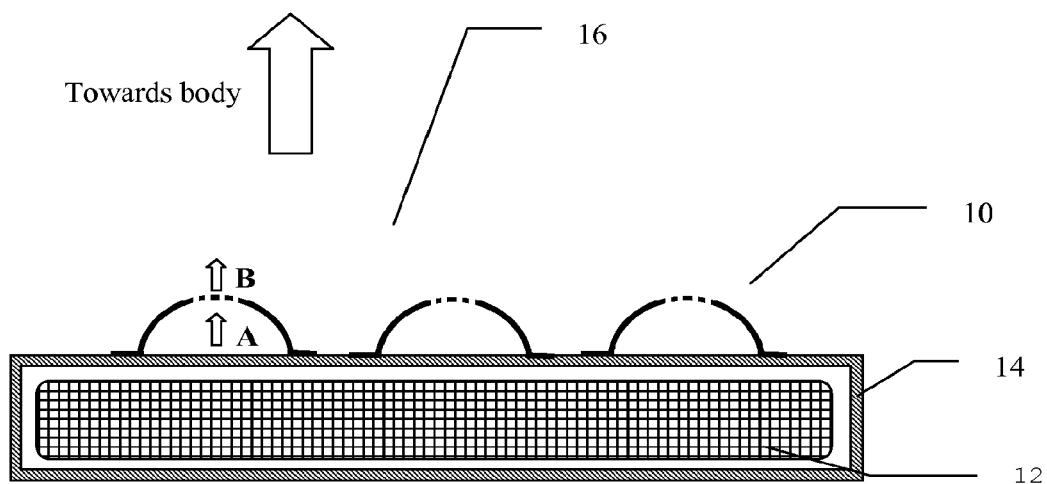
FIG. 2 is a side view of a heat treatment insert having thermally conductive massaging members with moisture conduit apertures.

The thermally conductive component can be rigid, or soft and compressible. In embodiments employing the thermally conductive component to deliver a massaging sensation, the massaging elements of the thermally conductive component are preferably rigid enough to maintain their shape when pressed against the skin. The raised portions of the thermally conductive component can be solid, hollow, or filled with conductive or non-conductive material. FIG. 2 illustrates an embodiment in which the raised portions 16 are provided with apertures to enable the release of one or more agents retained therein. The agents can be released either as a result of heat generated by thermal reservoir 12 or by the removal of one or more covering layers (not shown). In one embodiment, the interior surfaces of the raised portions of the thermally conductive component are in direct contact with the thermal fill material. In one embodiment, the thermally conductive component is filled with metal pellets. In certain embodiments, the side of the thermal reservoir which does not contain the thermally conductive component (i.e. the opposite side) is layered with a rigid portion or backing which allows the reservoir to maintain its shape upon placement into the garment. In one embodiment the rigid portion or backing may be constructed of a non-thermally conductive material such as but not limited to a plastic, polypropylene or polyethylene. In one embodiment the rigid portion or backing is layered on the side of a non-woven bag which contains an exothermic heating composition.

Another aspect of the present invention relates to methods for treating or managing pain, particularly muscle or joint pain, in humans. While heat, and massage have long been recognized as effective modalities for managing pain, the thermal insert of the present invention, in the embodiment wherein the thermally conductive component has at least a portion of its surface raised above the plane of the thermally active component, provides a means for delivering heat, along with a massaging sensation to the user. Compared to other methods of providing heat and massage, the method of the present invention is advantageously portable, wearable, and long lasting, with minimal effort required on the part of the user. An additional benefit of the massaging action of the thermal insert of the present invention is the further increase in blood flow to the affected area, facilitating the oxygenation, and removal of waste from the affected tissue. Yet another benefit of the massaging action of the thermal insert of the present invention is the sensory cue to remind the user the product is working. Sensory cues can improve patient compliance with a treatment regimen. One such regimen includes the wearing of the thermal insert of the present invention in close contact with the skin (either via a garment or patch) for from about 1 hour to about 16 hours. For example, a user can wear the thermal insert for from about 4 hours to about 8 hours, or from about 8 hours to about 12 hours, or from about 8 hours to about 16 hours, providing heat to the affected muscles or joints while simultaneously engaging in work or leisure activities.

In the therapeutic use of the thermal inserts of the present invention, the thermally conductive component(s) are in contact with the body of the user, either directly contacting the skin, or contacting the body through clothing or garments worn by the user. Simultaneously the thermally conductive component(s) are in contact with the thermal insert. The thermally conductive component(s) serve to effectively transfer or re-distribute heat or cold from the thermal inserts to the individual's body. In addition, thermally conductive component(s) create a non-uniform thermal sensations on the body or on the skin in case of direct application to skin, whereby body or skin areas in immediate contact with the thermally conductive component experience much stronger sensations of heat or cold relative to the adjacent areas.

In one embodiment, the thermally conductive member is substantially free of activated carbon, e.g. less than 0.1% by weight of the fill of the thermally conductive component.

In one embodiment (not shown), the interior cavities created by raised portions of the thermally conductive component are filled with substances that are capable of retaining heat for extended periods of time, such as thermal beads, encapsulated water, wax, phase change materials, ceramics, sand, grains, rice, wheat, corn, etc. Even after the chemical formulation inside the thermally active component stops delivering or generating heat, the substances that are capable of retaining heat for extended periods of time inside the thermally conductive component can continue releasing or absorbing heat for extended periods of time. Additionally, in case of accidental overheating of the chemical formulation inside the thermally active component, said substances are capable of absorbing the excess heat thus providing protection form overheating.

Advantageously and beneficially, the space around the raised portions of the thermally conductive component is available for removal and evaporation of sweat and provides for areas of the body or skin not in contact or not covered by any implement. Additionally, the thermal contrast (temperature difference between the skin and device) delivered to the body can be much higher when a thermally conductive component transferring heat and transferring cold is immediately adjacent to the body. This contrast can be achieved without significant losses of thermal energy due to heat transfer. In one embodiment, the thermal reservoir is a thermal pack.

Figure 1B:
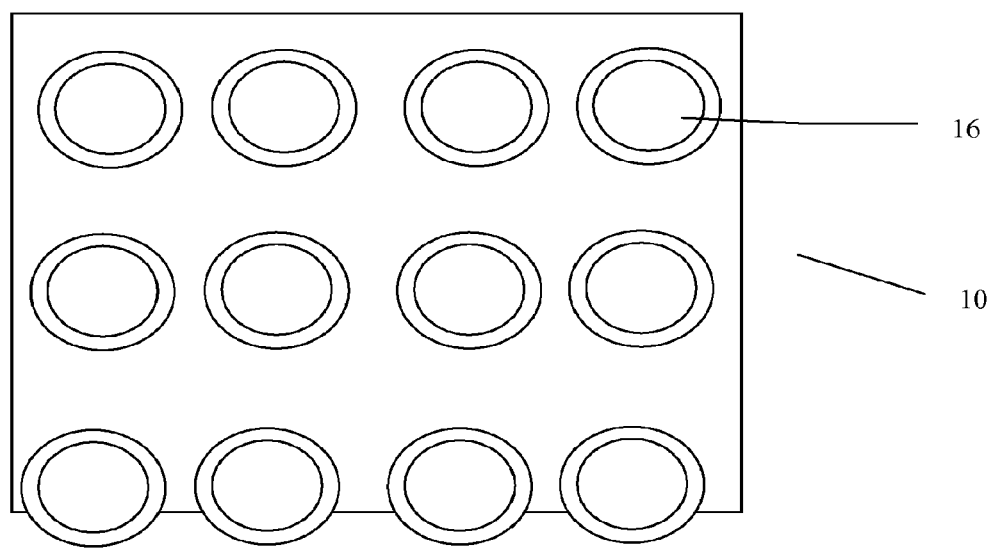
FIG. 1B is a top view of a heat treatment insert having thermally conductive massaging members.

The number of the thermally conductive component(s) per single thermal pack can vary from one to several. In one embodiment, from 6 to 30 or more thermally conductive components are installed on one bed or thermal pack. FIG. 1B exemplifies a device 10 having twelve conductive components 16. In one embodiment the dimensions of the thermally conductive components have a width from about 5 millimeters to about 50 millimeters, e.g. from about 7 millimeters to about 20 millimeters. In one embodiment, the dimensions of the thermally conductive components have a height from about 5 millimeters to about 50 millimeters, e.g. from about 7 millimeters to about 20 millimeters. As best illustrated in FIG. 1A, height is measured from the surface of device 10 to the apex of the thermal conductive component 16.

In embodiments wherein the shape of the thermally conductive components are semi-spherical, the diameter, which is equal to the width of the component, is from about 5 millimeters to about 50 millimeters, e.g. from about 10 millimeters to about 30 millimeters. In this embodiment the radius of the semi-spherical component, which is equal to the height, is from about 2.5 millimeters to about 25 millimeters, e.g. from about 5 millimeters to about 20 millimeters. Circular thermal conductive components 16 are shown in FIG. 1B.

In embodiments wherein the shape of the thermally conductive components are elliptical, the diameter, which is equal to the maximum width of the component, is from about 5 millimeters to about 50 millimeters, e.g. from about 10 millimeters to about 30 millimeters. In this embodiment the height of the elliptical component, is from about 2.5 millimeters to about 25 millimeters, e.g. from about 5 millimeters to about 20 millimeters.

In certain embodiments, the thermally conductive components can be defined by the volume of the internal space of the component. In certain embodiments, the internal volume of a thermally conductive component can be from about 0.01 milliliters to about 50.00 milliliters, e.g. from about 0.03 milliliters to about 33.00 milliliters, e.g. from about 0.10 milliliters to about 2.00 milliliters.

In one embodiment, wherein more than one thermally conductive components is present in the device, all thermally conductive components have the same height, while in another embodiment, some thermally conductive components are higher and some are lower, for example a first portion of the thermally conductive components are about 5 millimeters to about 10 millimeters high, while a second portion are about 10 millimeters to about 15 millimeters high, while an optional third portion are about 15 millimeters to about 20 millimeters high.

The thermal device can be of any shape and size suitable for wearing next to the skin of a human, and can be produced commercially in any shape and size that can be die cut. For example, thermal insert 10 can be round, triangular, square rectangular, pentagonal, hexagonal, etc. In one embodiment, at least one dimension of the thermal insert is from about 1 inch to about 30 inches. In one particular embodiment, thermal reservoir 12 has a triangular shape with a width from about 2 to about 6 inches, and overall length from about 2 to about 12 inches.

In certain embodiments, the thermal device can be substantially flat with the thickness of the device ranging from about 2 millimeters to about 30 millimeters, and the other dimensions of the insert ranging from about 24 millimeters to about 720 millimeters.

We claim:

1. A portable thermal device to be worn in close proximity to skin of a user comprising:
    a) a thermal reservoir comprising an enclosure and a thermal composition that generates a temperature contrast of at least about 10 degrees Celsius relative to a surface temperature of said skin, wherein the thermal composition comprises iron powder; and
    b) at least one thermally conductive component,
        i. wherein the at least one thermally conductive component is in temperature communication with the thermal reservoir and is positioned between the thermal reservoir and the skin,
        ii. wherein the at least one thermally conductive component has at least a portion of its surface raised above a plane of the thermal reservoir and through a portion of an interior of the enclosure that forms an exterior surface of the portable thermal device,
        iii. wherein the at least one thermally conductive component has an interior cavity created by a raised portion of the thermally conductive component that is filled with a substance capable of retaining or absorbing heat,
        iv. wherein the at least one thermally conductive component has thermal conductivity of about 10 W/mK to about 250 W/mK;
        v. wherein the at least one thermally conductive component has a width from about 5 millimeters to about 50 millimeters and a height from about 5 millimeters to about 50 millimeters; and
        vi. wherein the at least one thermally conductive component provides a temperature change sensation and a massaging sensation when placed in close proximity to said skin.

2. A therapeutic device comprising a portable thermal device according to claim 1 and a wearable garment having at least one pocket for holding the portable thermal device.

3. The therapeutic device of claim 2 wherein the shape(s) of the pockets are substantially the same shape as the corresponding portable thermal device.

4. The therapeutic device of claim 2 wherein the garment is conformable to fit over the shoulder, back, knee, or elbow of a human.

5. The therapeutic device of claim 2, wherein the garment is re-usable.

6. The therapeutic device of claim 2, wherein the garment is disposable.

7. The portable thermal device of claim 1, wherein the at least one thermally conductive component has a rounded shape.

8. The portable thermal device of claim 7, wherein the at least one thermally conductive component has rounded edges and rotates around a supporting element or within a socket.

9. The portable thermal device of claim 1, wherein the at least one thermally conductive component has a thermal conductivity of at least about 100 W/mK.

10. The portable thermal device of claim 1, wherein the at least one thermally conductive component has a thermal conductivity from about 150 W/mK to about 250 W/mK.

11. The portable thermal device of claim 1, wherein the thermally conductive component is composed primarily of a metal.

12. The portable thermal device of claim 1, wherein the thermally conductive component comprises at least one element selected from the group consisting of conductive textiles, composites, plastics, polymers, rubber, ceramics and mixtures thereof.

13. The portable thermal device of claim 1, in which the thermal composition emits heat from about 1 to about 10 degrees Celsius above the skin surface temperature of a human, when worn next to the skin of a human.

14. The portable thermal device of claim 1, in which the temperature of the thermal composition is from about 1 to about 100 degrees Celsius lower than that of the surface of human skin.

15. The portable thermal device of claim 1, wherein the thermally conductive component maintains a temperature of at least about 40 degrees Celsius from about 4 to about 16 hours when worn next to the skin of a human.

16. The portable thermal device of claim 1, wherein the thermally conductive component maintains a temperature of at least about 40 degrees Celsius for at least about 10 hours when worn next to the skin of a human.

17. A method of providing a massaging sensation together with heat to a patient comprising providing the portable thermal device of claim 1 in a garment for holding said thermal device and placing said garment in close proximity to the user's skin.

18. A method for treating muscle aches and pains in a human, comprising wearing the portable thermal device of claim 1 for a time period of about 1 hour to about 16 hours.

* * * * *